United States Patent
Ursella et al.

(10) Patent No.: US 10,739,329 B2
(45) Date of Patent: Aug. 11, 2020

(54) METHOD AND APPARATUS FOR NON-DESTRUCTIVE INSPECTION OF A LOG TO IDENTIFY INNER ZONES THAT ARE FREE OF BLUESTAIN

(71) Applicant: MICROTEC S.R.L., Bressanone (IT)

(72) Inventors: Enrico Ursella, Mestre (IT); Enrico Vicario, Martellago (IT)

(73) Assignee: MICROTEC S.R.L., Bressanone (IT)

( * ) Notice: Subject to any disclaimer, the term of this patent is extended or adjusted under 35 U.S.C. 154(b) by 256 days.

(21) Appl. No.: 15/953,704

(22) Filed: Apr. 16, 2018

(65) Prior Publication Data

US 2018/0313809 A1 Nov. 1, 2018

(30) Foreign Application Priority Data

Apr. 26, 2017 (IT) .......................... 102017000045342

(51) Int. Cl.
*G01N 33/46* (2006.01)
*G01N 23/046* (2018.01)

(52) U.S. Cl.
CPC ........... *G01N 33/46* (2013.01); *G01N 23/046* (2013.01); *G01N 2223/619* (2013.01)

(58) Field of Classification Search
CPC . G01N 2223/619; G01N 23/046; G01N 33/46
See application file for complete search history.

(56) References Cited

U.S. PATENT DOCUMENTS

| | | |
|---|---|---|
| 9,063,061 B2 | 6/2015 | Oden et al. |
| 9,241,446 B2 | 1/2016 | De Seixas Boavida Ferreira et al. |

(Continued)

FOREIGN PATENT DOCUMENTS

| | | |
|---|---|---|
| EP | 2343536 A1 | 7/2011 |
| EP | 2381247 A1 | 10/2011 |

(Continued)

OTHER PUBLICATIONS

Metzler, B., et al., "Comparing Norway Spruce and Silver Fir Regarding Impact of Bark Wounds", Forest Ecology and Management, Elsevier, Amsterdam, Netherlands, vol. 274, Feb. 19, 2012, pp. 99-107.

(Continued)

*Primary Examiner* — Chih-Cheng Kao
(74) *Attorney, Agent, or Firm* — Pearne & Gordon LLP

(57) ABSTRACT

This invention relates to a method for non-destructive inspection of a log (1) to identify inner zones of sapwood (14) of the log (1) that have not been attacked by fungi that cause bluestain in the wood. The method comprises a first step of carrying out a tomographic scan of the log (1) to be inspected using X-ray beams that pass through the log (1) and a second step of obtaining a three-dimensional representation of the log (1) that is representative of the local moisture content of the log, the local moisture content being correlated with attenuation of the X-ray beams through the log. The method comprises the step of processing the three-dimensional representation of the log (1) to identify inner regions (145) of the log (1), in which the local moisture content is greater than or equal to a moisture threshold value for a spatial extent greater than an extent threshold. The moisture threshold value corresponds, for trees of the same species as the log (1), to a sapwood (14) with local moisture content such that it excludes the growth of fungi that cause bluestain in the wood. Each inner region (145) identified in this way is classed as a sapwood (14) zone free of bluestain. This invention also relates to a procedure for obtaining one or more wooden products from a log (1), as well as an apparatus for carrying out a non-destructive inspection of a log (1).

18 Claims, 2 Drawing Sheets

(56) References Cited

U.S. PATENT DOCUMENTS

| | | | |
|---|---|---|---|
| 2011/0274239 A1 | 11/2011 | Giudiceandrea | |
| 2013/0003925 A1 | 1/2013 | Oden et al. | |
| 2014/0234438 A1* | 8/2014 | De Seixas Boavida Ferreira ....... | G01N 23/046 424/616 |
| 2016/0040933 A1* | 2/2016 | Stanish ................ | F26B 25/225 34/427 |
| 2019/0227049 A1* | 7/2019 | Narasimhan .......... | G06T 7/0004 |

FOREIGN PATENT DOCUMENTS

| | | |
|---|---|---|
| IT | BZ2011A000026 A1 | 12/2012 |
| WO | 2012052506 A1 | 4/2012 |

OTHER PUBLICATIONS

Van Den Bulcke, J., et al., "Three-Dimensional Imaging and Analysis of Infested Coated Wood With X-Ray Submicron CT", International Biodeterioration and Biodegradation, Elsevier, Amsterdam, Netherlands, vol. 61, No. 3, 2008, pp. 278-286.

* cited by examiner

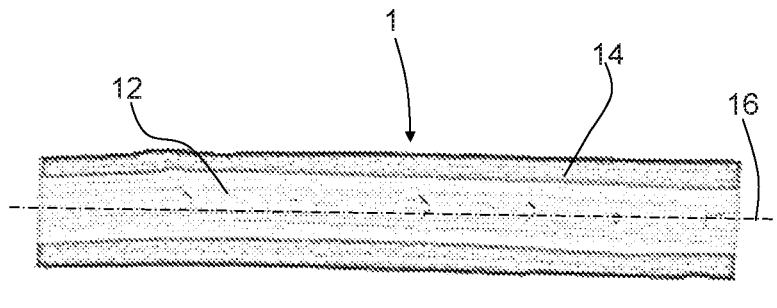
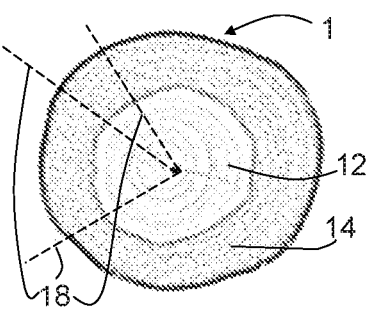
FIG. 3  FIG. 4
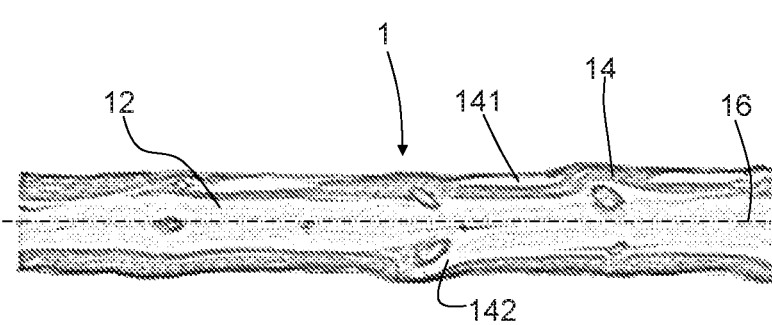
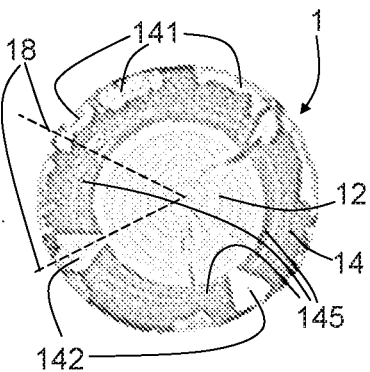
FIG. 5  FIG. 6
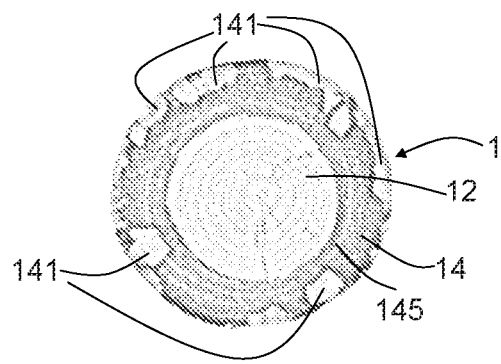
FIG. 7

METHOD AND APPARATUS FOR NON-DESTRUCTIVE INSPECTION OF A LOG TO IDENTIFY INNER ZONES THAT ARE FREE OF BLUESTAIN

CROSS-REFERENCE TO RELATED APPLICATION

The present application claims the benefit of Italian Patent Application No. 102017000045342 filed on Apr. 26, 2017, which is incorporated herein by reference in its entirety.

DESCRIPTION

This invention relates in general to the timber and log processing sector for obtaining wood usable for making products of any kind.

In particular, this invention relates to a method for non-destructive inspection of a log to identify inner zones of sapwood of the log that have not been attacked by fungi that cause bluestain in the wood. This invention also relates to an apparatus for carrying out that non-destructive inspection.

It is well known that the quality of wood depends both on the raw material and on the production processes applied to it. Specifically, the raw material is constituted of logs from trees cut down.

In aesthetic terms, the quality of wood may be compromised by a natural discoloration process caused by attacks by fungi. Amongst the various types of attack by biological factors, aesthetic quality is particularly compromised by fungi which attack the sapwood of the log, turning it a bluish or grey-green color. This phenomenon is well known in the sector as "bluestain". It is usually due to specific saprophytic fungi.

The products obtained from wood affected by bluestain are considered to be of low quality aesthetically, despite their mechanical properties not being compromised. Wood affected by bluestain is, therefore, to be considered a reject or, in any case, a material of considerably lower commercial value.

According to some prior art methods, bluestain in wood can be prevented by keeping the cut logs wet during hot seasons, or by means of antiseptic treatments on cut logs, or by sawing the logs immediately after cutting and then drying the boards obtained in that way in ovens, so as to bring them to a moisture content of around 12%.

In other cases, the decision is made to completely suspend wood production for high quality applications in hotter months, during which the growth of fungi that cause bluestain is more likely.

However, it must be considered that an attack by fungi may occur even on the living tree, before it is cut down to obtain the log, and therefore, the prior art methods indicated above would be ineffective if bluestain were already present.

Therefore, when cutting logs, efforts are made to assign logs potentially affected by bluestain to the production of boards for uses in which the aesthetic value is not important (for example, wood for construction). For this reason, operators carry out a visual inspection of the logs, although often visual inspection is not very effective.

In any case, the prior art methods do not allow objective assessment of whether or not a log is free of bluestain. Therefore, there is the risk that zones of bluestain are found in boards sawn from a log that was thought to be healthy. That involves considerable disadvantages in terms of the production process, both as regards quality control on the products obtained and concerning production rejects and the related costs.

Starting with the disadvantages of the prior art, this invention was devised to enable assessment of whether or not a cut log could have inner zones affected by bluestain and, if so, where those zones affected by bluestain could be.

That is achieved by means of a method for non-destructive inspection as described in the appended claims, as well as by means of an apparatus as claimed.

The method according to this invention is useful in particular for identifying which parts of a log are definitely healthy and therefore usable for cutting products with aesthetic value, and which parts have, in contrast, potentially been attacked and so must be intended for products with no aesthetic requirements.

With its experience in the sector, in particular relating to trees of resinous species (such as fir, spruce, conifers in general), the Applicant and/or the inventors have verified that the sapwood attacked by fungi that cause bluestain usually has a moisture percentage that is less than a normal moisture value, where "normal" means the moisture detected, for example, in healthy logs, recently cut, of trees of the same species as the log in question. The normal moisture value may vary considerably from one species to another, and therefore must be assessed on a case by case basis.

The Applicant and/or the inventors have verified that bluestain is never present in parts of the sapwood in which the moisture has remained at the normal value and that, however, there are cases in which regions of sapwood have an abnormal moisture level (therefore, they are highly exposed to attack by fungi) but the log is healthy. The Applicant and/or the inventors have also verified that, even if a part of the sapwood is attacked by fungi, the presence of a zone with normal moisture between the zone attacked and the heartwood indicates that the propagation of the attack has stopped before reaching the heartwood.

In practice, according to what was verified by the Applicant and/or the inventors, the attack by fungi that cause bluestain starts from the outer surface of the log and extends towards the center of the log. Moreover, the attack is associated with zones of the sapwood that have an abnormal moisture level, that is to say, sapwood that is dried compared with the normal moisture level.

On this basis, the inventors have developed the method for non-destructive inspection according to this invention. Specifically, the method is based on a tomographic scan of the log to be inspected and uses the principle of tomography to enable indirect measurement of the local moisture content in the inner regions of the log. In particular, the tomographic scan enables measurement of the attenuation of the X-ray beams passing through the log and that attenuation is quantifiable for example in terms of radio-density, which is directly correlated with moisture content. Therefore, it is possible to assess which zones have normal moisture and which have abnormal moisture and, consequently, to establish which inner regions of the log are free of bluestain and which inner regions could, in contrast, present risks of bluestain. The information obtained in that way is usable, for example, for optimizing a log cutting pattern and/or for assigning the log a class or grade in terms of quality and economic value.

The non-destructive inspection method according to this invention has been developed in particular for logs from trees of resinous species, however, it is also applicable to other species.

Further features and the advantages of this invention are more apparent in the detailed description below, with reference to a preferred, non-limiting embodiment of a method and an apparatus for non-destructive inspection of a log. Reference will be made to the accompanying drawings, in which:

FIGS. 3 and 4 are respectively a longitudinal sectional view and a cross-sectional view of a tomographic image obtained for a first example of a log, FIGS. 3 and 4 being in different scale to one another;

FIGS. 5 and 6 are respectively a longitudinal sectional view and a cross-sectional view of a tomographic image obtained for a second example of a log, FIGS. 5 and 6 being in different scale to one another;

FIG. 7 is cross-sectional view of a tomographic image obtained for a third example of a log.

Figure 1:
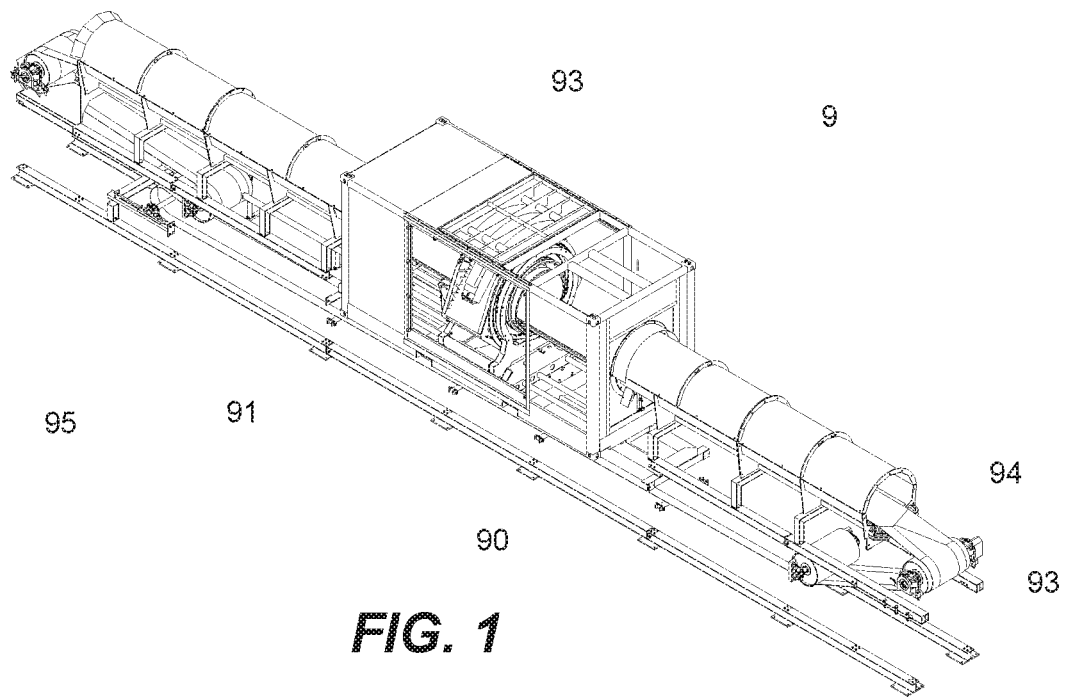
FIG. 1 is a perspective view of an example of a tomography apparatus usable for this invention.
Figure 2:
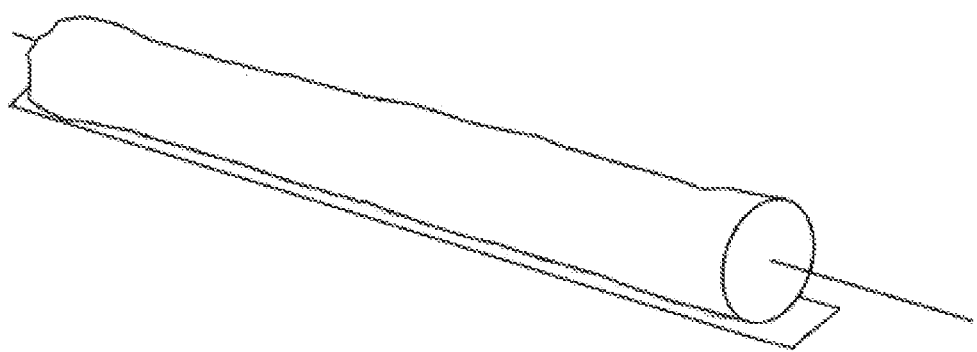
FIG. 2 is a simplified view of a log moved in such a way that it can be subjected to a tomographic scan during a step of the method according to this invention.

With reference to the above-mentioned figures, a log has been generically labelled with the reference character 1 and a tomography apparatus for carrying out a tomographic scan of the log 1 has been labelled with the reference character 9. Tomography apparatuses of this type are already known in themselves and are described, for example, in the publication of European patent application No. EP2381247A1 and in Italian patent application No. BZ2011A000026, both by this Applicant, and will not be described in detail herein.

The tomography apparatus 9 comprises a supporting structure 90, a tomograph 91 and a movement system 92 for moving a log 1 along a substantially straight movement path. The tomograph 91 comprises X-ray emitters and respective X-ray receivers.

In particular, the tomograph 91 is positioned at an intermediate position of the movement path and is positioned at the center of the tomography apparatus 9 in a containment structure 93, some walls of which have been cut away for clarity in FIG. 1. The movement system 92 is structured for causing, during operation, the log 1 to pass through the tomograph 91. In particular, the movement system 92 comprises a conveyor belt 94 on which, during operation, the log 1 to be subjected to a tomographic scan can be positioned. The conveyor belt 94 runs along the movement path in such a way that it passes through the tomograph 91. To avoid influencing the result of the tomographic scan, the conveyor belt 94 may be made of a material that is substantially transparent to X-rays.

According to known methods, during the tomographic scan X-ray beams produced by the X-ray emitters pass through the log 1 and are received by the respective receivers. Due to their having passed through the log, the X-ray beams received by the receivers are attenuated compared with the X-ray beams emitted. The attenuation depends on the chemical—physical properties of the material passed through along the path. An electronic processing unit 95 is configured to process the information obtained by the tomograph 91 during the tomographic scan, in order to obtain a three-dimensional representation of the log in which, for example, a local radio-density value is assigned to each inner point or region of the log 1.

In the case of wood, thanks to the homogeneity of the attenuation coefficients of water and carbon, for example at voltages of 100-200 kV, it is possible to find a close correlation between the attenuation of the X-rays and the density of the material passed through. Since the density of the wood depends on its moisture content, it is possible to correlate the moisture content with the attenuation of the X-rays and in particular with the radio-density.

It is known that a log obtained from a tree has a longitudinal central core, called heartwood, that is a part free of living cells and having a supporting function, and an outer part, called sapwood, which coaxially surrounds the heartwood. When the tree is alive, the sapwood is formed of living cells and sap flows through it.

In the accompanying figures, the heartwood is labelled with the reference character 12, the sapwood is labelled 14 and a longitudinal central axis of the log 1 is labelled 16.

As already described above, there are fungi which attack wood and cause bluestain in the wood. In particular, those fungi that cause bluestain attack the sapwood. In contrast, the heartwood is usually resistant to attack by such fungi thanks to chemical substances which are developed by the tree at the heartwood region. Therefore, the heartwood may be considered free of the risk of bluestain.

The attack on the sapwood by the fungi usually starts from the outer periphery of the sapwood, that is to say, from the part facing the bark.

The wood of the log has a moisture content that is not the same throughout the whole log. The moisture content of wood is usually expressed, in percentage terms, as the ratio of the mass of water contained in a volume of wood to the dry mass of that same volume of wood. The moisture content may therefore have values greater than 100%.

The heartwood has a moisture content that is usually less than the moisture content of the sapwood, at least when the tree is alive and healthy. For example, the heartwood is substantially dry and may have a moisture content of 30%, whilst the healthy sapwood (that is to say, not attacked by fungi) may have a moisture content of at least 60%, up to even 150% or higher.

For trees of resinous species, a division between heartwood and sapwood is particularly clear to the naked eye in cross-sections of the log. The method according to this invention is intended in particular for logs from trees of resinous species (such as fir, spruce, conifers in general), however it is also applicable to other species.

According to the experience of the Applicant and/or the inventors, the zones of sapwood which are attacked by the fungi that cause bluestain correspond to zones which have a moisture content which is less than the normal moisture content and which is closer to the moisture content of the heartwood. Zones of the sapwood with a moisture content that has remained at a normal value are not subject to bluestain. Therefore, it is possible to define a moisture threshold value which is such that, in a zone of sapwood with a moisture content greater than or equal to that threshold value, the growth of fungi that cause bluestain may be ruled out.

Basically, according to the experience of the Applicant and/or the inventors, zones which remain sufficiently moist are free of the fungi that cause bluestain. This is experimental data, irrespective of the causes or effects. In fact, on one hand local drying may be a cause of the growth of fungi, but on the other hand the growth of fungi may promote local drying of the adjacent zones, destroying the walls of the vessels of the trunk or log. Causes and effects aside, the significant aspect for this invention is the correlation between the "normal" moisture content and the absence of bluestain.

The moisture threshold value that is sufficient to exclude the growth of fungi that cause bluestain in wood may vary significantly from one species of tree to another, like the moisture content in the sapwood. However, the Applicant and/or the inventors have verified that, in logs obtained from trees cut down (in particular for resinous species), zones with a moisture content that is approximately the mean of the moisture of the heartwood and the moisture of the healthy sapwood are quite rare and tend to reach the moisture content of the heartwood in rather short periods. In other words, it is possible to quite clearly distinguish between zones of sapwood which are free of bluestain and zones of sapwood potentially affected by bluestain, based on their moisture content.

This means that, for the purposes of this invention, the moisture threshold value may be an approximate value.

This invention relates to a method for non-destructive inspection of a log 1 to identify inner zones of sapwood 14 of the log 1 that have not been attacked by fungi that cause bluestain in the wood.

The method for non-destructive inspection comprises first the step of carrying out a tomographic scan of the log 1 to be inspected using X-ray beams that pass through the log and obtaining a three-dimensional representation of the log 1 that is representative of the local moisture content of the log. As already mentioned above, the local moisture content is correlated with the attenuation of the X-ray beams through the log 1 and therefore is information obtainable from the data produced by the tomography apparatus 9 during the tomographic scan.

That three-dimensional representation, which is preferably in digital format and can be processed by the electronic processing unit 95, may be expressed as a graphical image but could be expressed in table or matrix form. Basically, that three-dimensional representation establishes a correspondence between the coordinates of points or regions of the log and a quantity that can be traced to the moisture content at that point or region.

The term "local content" therefore means that the value of the quantity refers to a specific point or small region of interest (the size of the small region corresponding for example to the spatial resolution of the tomography apparatus 9), not to a mean value calculated for the whole log or the whole of the sapwood.

The three-dimensional representation of the log 1 is processed to identify one or more inner regions of the log 1 in which the local moisture content is greater than or equal to a threshold moisture value. The threshold moisture value corresponds to a sapwood 14 with local moisture content such that it excludes the growth of fungi that cause bluestain in wood, for trees of the same species as the log 1 to be inspected.

In particular, inner regions are considered in which the local moisture content is greater than or equal to the threshold moisture value in a spatial extent that is greater than an extent threshold. The introduction of an extent threshold is useful for omitting single points or small isolated regions in which the moisture content could (erroneously) be greater than the threshold only because of the measurement uncertainty, in which small dimensions are not sufficient to exclude bluestain towards the centre of the log, or in which in any case the dimensions are too small for the respective piece of log to be usable.

Said inner regions with moisture threshold greater than or equal to the moisture threshold in a sufficient extent are first inner regions which are classed as zones of sapwood 14 free of bluestain. In fact, as already indicated above, moisture greater than the threshold is correlated with the absence of attack by fungi that cause bluestain.

Any remaining inner regions of the log 1, having moisture that is less than the moisture threshold and/or having a spatial extent that is less than the extent threshold, are second inner regions. Those second inner regions may be at risk of bluestain, at least as regards their portion of the sapwood 14. The moisture threshold value may be different from one species to another.

It may be selected based on pre-existing experimental data, or it could be selected for example as a mean value of the moisture content of the heartwood and the moisture content of the sapwood for trees of the same species, which are healthy and have just been cut down. Alternatively, the moisture threshold value could be selected as a fixed value that may approximately be expected for all tree species for which the inspection apparatus is intended. For example, that threshold value could be a moisture value of 45%.

If necessary, the moisture threshold value might not be a single value for the whole log to be inspected: different threshold values could be considered for different regions of the log. For example, if the log is assessed by inspecting a sequence of cross-sections of the log, for each cross-section a respective moisture threshold value could be adopted, as described in further detail below.

In FIGS. 3 to 7, darker regions correspond to a higher moisture content and lighter regions correspond to a lower moisture content.

FIGS. 3 and 4 respectively show a longitudinal section and a cross-section of the three-dimensional representation of a log 1 that is completely healthy.

As can be seen, the zone of heartwood 12 is clearly distinct from the zone of sapwood 14, which does not have any substantial variations in moisture inside it. Therefore, in this case, the whole of the sapwood 14 is classed as a first inner region that is free of bluestain.

FIGS. 5 and 6 respectively show a longitudinal section and a cross-section of the three-dimensional representation of a log 1 which has been profoundly attacked by fungi that cause bluestain. As can be seen, in the zone of sapwood 14 there are several regions 141, 142 which have a moisture content that is less than that of the other regions of the sapwood, that moisture content being similar to that of the zone of heartwood 12. Some regions 142 with moisture content which is less than the moisture threshold even extend as far as the heartwood 12 and at them the border between the heartwood 12 and the sapwood 14 is substantially indistinguishable. In those regions 141, 142, in which the moisture content is below the threshold value, the wood could be affected by bluestain.

Therefore, for the log 1 of FIGS. 5 and 6 the sapwood 14 has first inner regions (several labelled 145) which are classed as free of bluestain and second inner regions 141, 142 which are classed as at risk of bluestain.

FIG. 7 shows a cross-section of the three-dimensional representation of a log 1 which has been partly attacked by fungi that cause bluestain, but to a lesser degree than the log in FIGS. 5 and 6. In this case too, in the zone of sapwood 14 there are several regions 141 which have a moisture content that is less than that of the other regions of the sapwood and similar to the heartwood 12. However, none of the regions 141 extend as far as the heartwood 12, which is therefore surrounded by a continuous ring 145 of sapwood 14 with moisture content greater than the threshold. In this case, the border between the heartwood 12 and the sapwood 14 is clearly distinguishable.

Therefore, for the log 1 of FIG. 7 the sapwood 14 has a first inner region that is classed as free of bluestain, encloses the heartwood 12 and extends in a large part of the sapwood 14. However, there are second inner regions 141 present which are classed as at risk of bluestain.

As indicated above, it has been verified that attack by fungi that cause bluestain and local drying of the sapwood propagate from the outside (that is to say, from the surface of the sapwood 14 facing the bark of the log) towards the center of the log 1. Therefore, moving along radial lines 18, the presence of a first region unaffected by bluestain suggests that the more internal part of the sapwood is also unaffected by bluestain. This may be seen, for example, in FIGS. 5 to 7. Moreover, as already indicated, the heartwood 12 is in itself resistant to attack by fungi.

Consequently, when a first inner region that is free of bluestain is identified, it is also possible to class the zone that extends radially between that first inner region and the longitudinal central axis 16 as being a zone free of bluestain. That enables the minimizing of the parts of the log 1 to be rejected because of the potential presence of bluestain.

Moreover, considering that the heartwood 12 is in itself protected against bluestain, it is useful to be able to identify a border between the heartwood 12 and the sapwood 14 even in cases in which the second inner regions 142 with reduced moisture extend as far as the heartwood 12. That may be achieved as follows.

For each first inner region 145 identified as being free of bluestain, a piece of border is interposed between the first inner region 145 and the longitudinal central axis 16, at a change in the moisture content between a value greater than or equal to the moisture threshold value and a value less than the moisture threshold value. In fact, it is important to consider that the heartwood 12 has a moisture content that is less than the moisture content of the healthy sapwood and is comparable to the moisture content of the sapwood potentially affected by bluestain. Therefore, for healthy first regions 145 bordering the heartwood 12, a variation in the moisture content at the border is observed.

Thus, it remains to define the position of the border for any second regions of sapwood 142 with a moisture content that is less than the threshold, which extend as far as the heartwood 12 and are therefore interposed between pieces of border established for the first regions 145. Since those second regions 142 could have a level of moisture that is not distinguishable from the heartwood, it may be the case that there is no observable change in moisture content at the border.

Therefore, for those second inner regions 142 a piece of border is established by interpolation of the pieces of border established for the first inner regions. It must be kept in mind that the sapwood 14 is practically coaxial to the heartwood 12. In fact, the heartwood is formed from old growth rings in the innermost part of the log. Therefore, the interpolation is performed using an interpolating curved surface having an axis substantially on the longitudinal central axis 16 of the log 1 (for example, a portion of a cylindrical surface with its axis on the central axis 16). Basically, the border is established by continuity.

Once the border of the heartwood 12 has been established, the zone corresponding to the latter can also be classed as free of bluestain.

It should be noticed that for the log of FIGS. 3 and 4 and for the log of FIG. 7 the border between heartwood 12 and sapwood 14 is definable without the need for interpolation, whilst interpolation would be necessary in the case of the log of FIGS. 5 and 6.

In some cases in which the sapwood 14 has very extensive second inner regions 142, it might not be possible to identify with certainty the border between the sapwood and the heartwood by applying the method described above. In such bad cases, the whole angular sector involved or even the whole log may, as a precaution, be considered at risk of bluestain.

Alternatively to the method described above, other methods, if necessary from the prior art, may be used to identify the border between heartwood 12 and sapwood 14.

As regards the extent threshold for the first inner regions to be classed as free of bluestain, this is, for example, a radial extent of at least 1 cm, in particular a radial extent of at least 2 cm. In other words, a region in which the moisture content is greater than the moisture threshold value is considered unaffected by bluestain if it extends towards the longitudinal central axis 16 for at least 1 cm or, with a more restrictive criterion, for at least 2 cm. If that region has a smaller extent, there is the risk that it is only a local irregularity and therefore, prudently, the region is classed amongst the second regions at risk of bluestain.

The extent threshold may also have an axial component (that is to say, parallel to the longitudinal central axis 16), in addition to the radial component. For example, in the axial direction too, the extent threshold could be at least 1 cm, in particular at least 2 cm.

For the purposes of this invention, the moisture content and the respective threshold do not necessarily have to be expressed in terms of the ratio of the mass of water contained in a volume of wood to the dry mass of the same volume of wood. They may be expressed in any other terms that depend on the moisture content and enable assessment of which zones have dried and which have remained moist.

In particular, in one embodiment of this invention the moisture content is expressed in terms of radio-density, which is a measure of the attenuation of the X-ray beams through the material and, in the case of a wooden log, is directly correlated with the moisture content. The radio-density is measured in Hounsfield units (HU), also called the "CT number", and is a quantity commonly used in tomography.

In the case of wood, the formula $HU=\rho-1000$, where $\rho$ is the density in kg per cubic meter, is a good approximation. The moisture content U is given by $U=100\times(\rho-\rho 0)/\rho 0$, where $\rho 0$ is the density of the dry wood for the species in question. For example, for spruce the density of the dry wood is around 450 kg/m$^3$.

Therefore, $\rho=\rho 0+U\times\rho 0/100$, and so $HU=\rho 0+U\times\rho 0/100-1000$.

That shows that the density (in kg/m$^3$) and the radio-density (in HU) are directly correlated with the moisture content.

For example, the moisture threshold value corresponds to a radio-density value that is approximately a mean value of the radio-density of the heartwood (for wood of the same species), measured in HU, and a radio-density of 0 HU. In fact, the Applicant and/or the inventors have verified that the radio-density of the sapwood that remained moist is, as an approximate value, around 0 HU. For conifers, the radio-density of the heartwood is roughly −500 HU.

Alternatively, considering that the radio-density of the sapwood that remained moist is roughly 0 HU and that the radio-density of the heartwood is noticeably less, the moisture threshold value may be selected as corresponding to a fixed radio-density value, for example −100 HU.

In general, as regards the step of processing the three-dimensional representation of the log to identify the regions in which the local moisture content is greater than or equal to a moisture threshold value, it should be noticed that this may be performed directly by comparing the local moisture values with the moisture threshold value, or indirectly by comparing other quantities which, being linked to the moisture content, enable the same result to be obtained.

As already discussed above, density or radio-density may be used in place of moisture content, since they are proportional to the latter. A moisture content threshold corresponds to a density or radio-density threshold.

Other related quantities may obviously be used for the same purpose.

For example, with reference to FIGS. 3 to 7, the quantity considered could be brightness; the distinction between moist zones (darker) and dried zones (lighter) may be made with reference to a brightness threshold, which corresponds to a moisture threshold.

In another example, the quantity considered could be the contrast (as the brightness contrast) between the adjacent growth rings. In fact, that brightness contrast appears less for the zones with high moisture and more for the dried zones. Again in this case, a brightness contrast threshold may be established which corresponds to a moisture threshold. In fact, the growth rings are formed by zones of wood with different density, alternating with each other: the early wood, which has larger channels suitable for containing a lot of water, and the late wood, which has smaller channels.

Due to the empty space of the channels, the dry density of the late wood is much greater than the dry density of the early wood. Consequently, for the heartwood and the zones of dried sapwood, in which the channels are empty or contain little water, it is possible to see the contrast between the rings of late wood and the rings of early wood in an image obtained from the tomographic scan. In contrast, for the zones of sapwood in normally moist conditions, the channels are full of water and therefore the density of the early wood is closer to (or, for some species, even greater than) the density of the late wood, thus the contrast between the rings of late wood and the rings of early wood is much less clear. Therefore, there is a link between the difference in contrast between the rings and the moisture content.

Finally, it should be noticed that, similarly to what was discussed above for the step of processing the three-dimensional representation of the log, also the step of examining the variation in the local moisture content may be carried out directly by comparing local moisture values with the moisture threshold value, or indirectly by comparing other related quantities.

In one embodiment, the step of processing the three-dimensional representation of the log 1 to identify the inner regions with local moisture content that is greater than or equal to the moisture threshold value is carried out by processing a plurality of cross-sections of the three-dimensional representation. Essentially, said processing step comprises the sub-steps of:

dividing the three-dimensional representation of the log 1 into a plurality of representations of cross-sections of the log (for example, those of FIGS. 4, 6 and 7). Representing a transversal slice of the log 1, each cross-section comprises a central zone of heartwood 12 and an annular zone of sapwood 14 that surrounds the central zone of heartwood 12;
  for each representation of a cross-section, examining the variation in the local moisture content of the annular zone of sapwood 14 from the outer periphery towards the center of the cross-section along a plurality of radial lines and checking, for each radial line, if the local moisture content is greater than or equal to the moisture threshold value for at least one contiguous stretch, said contiguous stretch having an extent greater than the extent threshold value (for example, at least 2 cm along a radial line);
  for each representation of a cross-section, classing said contiguous stretches as first inner regions that are zones of sapwood free of bluestain.

According to what is indicated above, each cross-section is examined along radial lines which pass through the sapwood and go towards the heartwood.

Several radial lines are shown in FIGS. 4 and 6, where they are labelled 18. In particular, said radial lines may be selected angularly equally spaced relative to the center of the cross-section of the log, so as to assess the whole cross-section in a regular way. For example, the radial lines are angularly equally spaced by approximately 1 sexagesimal degree from one another, therefore each cross-section is examined along 360 radial lines.

Basically, for each cross-section 360 equally spaced points are considered, all belonging to the surface of the log 1 and, proceeding from the outside towards the center of the cross-section, the data obtained from the tomographic scan (for example, the radio-density in HU) are analyzed. Upon encountering a sufficiently large contiguous zone along which the moisture content (or the radio-density) is greater than or equal to the predetermined threshold, the area between the contiguous zone and the center of the cross-section of the log is classed as free of bluestain. If, in contrast, the center of the cross-section of the log is reached without ever encountering a significant contiguous stretch with moisture (or radio-density) greater than or equal to the predetermined threshold, the whole angular sector is classed as potentially attacked by bluestain.

The division of the three-dimensional representation of the log 1 into a plurality of representations of cross-sections is performed with a predetermined longitudinal step. For example, the cross-sections considered are spaced from one another with a step that is less than or equal to 2 cm. In particular, the step is 1 cm and the entire length of the log is ideally divided into 1-cm slices.

As regards identification of the border between heartwood and sapwood, this may be performed for each representation of a cross-section. For the radial lines in which said contiguous stretch is present with moisture greater than the threshold value (first radial lines), a piece of border is interposed between the contiguous stretch and the center of the cross-section, at a change in the moisture content between a value greater than or equal to the moisture threshold value and a value less than the moisture threshold value.

For the other radial lines in which said contiguous stretch is not present (second radial lines), a piece of border is identified by interpolation of the pieces of border for the first radial lines, with an interpolating curve centered in the center of the cross-section (for example, an arc of a circle centered in the center).

By repeating for all of the cross-sections, it is possible to establish the border between heartwood 12 and sapwood 14 for the entire log 1. The region of heartwood 12 identified in this way may also be classed as a zone free of bluestain.

In some cases an attack by fungi or local drying could start from one of the cut ends of the log 1 (or from both ends), with longitudinal rather than radial propagation. In these cases, in the cross-sections closest to the cut ends there could be zones of bluestain even between the heartwood and the healthy parts of the sapwood. The method described above could provide results that are not completely precise for such cross-sections. If there is any suspicion of such longitudinal propagation, it may be appropriate to reject the respective stretch of log and/or check for the presence of any anomalies or inconsistencies in the results relating to the cross-sections closest to the cut end in question.

Returning to processing of a plurality of cross-sections of the three-dimensional representation, it should be noticed that the moisture threshold value may be a single value for the entire log, or for each representation of a cross-section a respective moisture threshold value may be selected.

In particular, the respective moisture threshold value may be selected on the basis of a statistical analysis of the moisture distribution (or, equivalently, the density distribution) in the representation of a cross-section. For example, for each cross-section the distribution of local moisture values is examined so as to calculate a first value for them at the 95th percentile (which corresponds to moist wood) and a second value at the 20th percentile (which corresponds to dried wood); the mean of the first and second values is taken as the moisture threshold value.

It is clear that the processing steps of the methods according to this invention relate to data processing that can be carried out by an electronic processing unit, automatically, by running a suitable computer program. Following application of the non-destructive inspection method described above to the log 1, once the zones 145 free of bluestain have been identified, the log can be sawn to obtain one or more products (for example, wooden boards or pieces of log) from the parts of the log that have been classed as free of bluestain.

This invention also relates to a procedure for obtaining one or more wooden products from a log 1, comprising a preliminary step of non-destructive inspection and a subsequent step of drawing up a cutting pattern that takes into account the zones of log 1 that have been classed as zones free of bluestain. The log 1 is then cut according to the cutting pattern in order to obtain the one or more products.

Basically, the results of the non-destructive inspection method according to this invention may be used for optimizing a cutting pattern for the log 1, for example for producing boards that are completely free of bluestain or only affected by bluestain in negligible or insignificant zones.

The results of the non-destructive inspection method according to this invention may be used for optimizing cutting of a log 1, so as to eliminate or separate pieces of log based on the distribution of the zones that are free of bluestain and the zones potentially affected by bluestain.

The results of the non-destructive inspection method according to this invention may be used to class or grade the log 1 based on the distribution of the zones that are free of bluestain and the zones potentially affected by bluestain. For example, that classification may be expressed in terms of dimensions of the maximum cylinder that can be inscribed in the zone that is free of bluestain. A quality level assessment may be assigned to the log 1 based on the results of the non-destructive inspection.

Finally, this invention also relates to an apparatus for carrying out said non-destructive inspection on a log 1. The apparatus comprises a tomography apparatus 9, suitable for carrying out a tomographic scan of the log 1 to be inspected, and an electronic processing unit (which can be the self-same electronic processing unit 95) configured for processing the data obtained from the tomographic scan as described above, in order to identify inner zones 145 of sapwood 14 of the log 1 which have not been attacked by fungi that cause bluestain in wood. Moreover, the electronic processing unit can identify the borders of the heartwood relative to the sapwood. The same electronic unit can draw up a cutting pattern for the log and/or perform other processing based on the distribution of the zones which are free of bluestain and of the zones potentially affected by bluestain.

This invention brings important advantages.

In particular, this invention is useful for preliminary assessment of which zones of a log 1 are free of bluestain and are therefore suitable for use for products with good aesthetic quality. That enables the use of logs to be optimized and, moreover, enables each log to be assigned a technical—commercial value based on an objective assessment of its state relative to possible attack by fungi that cause bluestain.

The invention described above may be modified and adapted in several ways without thereby departing from the scope of the appended claims.

All details may be substituted with other technically equivalent elements and the materials used, as well as the shapes and dimensions of the various components, may vary according to requirements.

The invention claimed is:

1. A method for non-destructive inspection of a log (1) to identify inner zones of sapwood (14) of the log (1) that have not been attacked by fungi that cause bluestain in the wood, the log (1) having a longitudinal central axis (16), a heartwood (12) that forms a longitudinal central core, and a sapwood (14) that coaxially surrounds the heartwood (12), the method comprising the steps of:
   carrying out a tomographic scan of the log (1) to be inspected using X-ray beams that pass through the log (1);
   obtaining a three-dimensional representation of the log (1) that is representative of the local moisture content of the log, the local moisture content being correlated with attenuation of the X-ray beams through the log;
   processing the three-dimensional representation of the log (1) to identify one or more first inner regions (145) of the log (1) in which the local moisture content is greater than or equal to a moisture threshold value for a spatial extent greater than an extent threshold, the moisture threshold value corresponding, for trees of the same species as the log (1), to a sapwood (14) with local moisture content such that it excludes the growth of fungi that cause bluestain in the wood;
   classing each first inner region (145) identified as a sapwood (14) zone free of bluestain, any remaining inner regions of the log (1) being second inner regions (141, 142).

2. The method according to claim 1, wherein, for each first inner region identified (145), the zone that extends radially between the latter and the longitudinal central axis (16) is classed as a zone free of bluestain.

3. The method according to claim 1, wherein the extent threshold includes a radial extent of at least 1 cm.

4. The method according to claim 3, wherein the radial extent is of at least 2 cm.

5. The method according to claim 1, comprising the further step of identifying a border between the heartwood (12) and the sapwood (14), wherein:
   relative to each first inner region identified (145), a piece of border is interposed between the first inner region (145) and the longitudinal central axis (16), the piece of border being established at a change in the moisture content between a value greater than or equal to the moisture threshold value and a value less than the moisture threshold value;

relative to each second inner region (142) that may be present, interposed between pieces of border established for said first inner regions (145), a piece of border is established by interpolation of the pieces of border established for said first inner regions (145), the interpolation using an interpolating curved surface having an axis substantially on the longitudinal central axis (16);

wherein the heartwood (12) may also be classed as a zone free of bluestain.

6. The method according to claim 1, wherein the step of processing the three-dimensional representation of the log (1) comprises the sub-steps of:

dividing the three-dimensional representation of the log (1) into a plurality of representations of cross-sections of the log, each cross-section comprising a central zone of heartwood (12) and an annular zone of sapwood (14) that surrounds the central zone of heartwood (12);

for each representation of a cross-section, examining the variation in the local moisture content of the annular zone of sapwood (14) from the outer periphery towards the center of the cross-section along a plurality of radial lines (18) and checking, for each radial line (18), if the local moisture content is greater than or equal to the moisture threshold value for at least one contiguous stretch, said contiguous stretch having an extent greater than the extent threshold value;

for each representation of a cross-section, classing said contiguous stretches as first inner regions (145) that are zones of sapwood free of bluestain.

7. The method according to claim 6, wherein said radial lines (18) are angularly equally spaced relative to the center of the cross-section of the log (1).

8. The method according to claim 7, wherein said radial lines (18) are angularly equally spaced by approximately 1 sexagesimal degree from one another.

9. The method according to claim 6, wherein said cross-sections are spaced from one another with a step that is less than or equal to 2 cm.

10. The method according to claim 9, wherein the step is of 1 cm.

11. The method according to claim 6, comprising the further step of identifying, for each representation of a cross-section, a border between the zone of heartwood (12) and the zone of sapwood (14), wherein:

for first radial lines in which said contiguous stretch is present, a piece of border is interposed between the contiguous stretch and the center of the cross-section, at a change in the moisture content between a value greater than or equal to the moisture threshold value and a value less than the moisture threshold value;

for second radial lines in which said contiguous stretch is not present, a piece of border is identified by interpolation of the pieces of border for the first radial lines with an interpolating curve centered in the center of the cross-section;

wherein the heartwood (12) may also be classed as a zone free of bluestain.

12. The method according to claim 6, comprising the step of selecting, for each representation of a cross-section, a respective moisture threshold value.

13. The method according to claim 12, wherein the respective moisture threshold value is selected on the basis of a statistical analysis of the distribution of moisture in the representation of a cross-section.

14. The method according to claim 1, wherein the moisture content is expressed in terms of radio-density, the radio-density being a measure of the attenuation of the X-ray beams and being directly correlated with the moisture content.

15. The method according to claim 14, wherein the radio-density is measured in Hounsfield units (HU) and said moisture threshold value corresponds to a radio-density value that is approximately a mean value of the radio-density of the heartwood (12), in HU, and a radio-density of 0 HU.

16. The method according to claim 14, wherein the radio-density is measured in Hounsfield units (HU) and said moisture threshold value corresponds to a radio-density value of −100 HU.

17. A procedure for obtaining one or more wooden products from a log (1), comprising the steps of:

applying to the log (1) the non-destructive inspection method according to claim 1;

drawing up a cutting pattern that takes into account the zones of log (1) that have been classed as zones free of bluestain;

obtaining said one or more wooden products by cutting the log (1) in accordance with the cutting pattern.

18. An apparatus for carrying out a non-destructive inspection of a log (1) to identify inner zones of sapwood (14) of the log (1) that have not been attacked by fungi that cause bluestain in the wood, the apparatus comprising a tomography apparatus (9) and an electronic processing unit (95), the tomography apparatus (9) being suitable for carrying out a tomographic scan of the log (1), the electronic processing unit (95) being configured for processing the data obtained from the tomographic scan according to the steps of the method of claim 1.

* * * * *